US008064660B2

(12) United States Patent  (10) Patent No.: US 8,064,660 B2
Leow et al.  (45) Date of Patent: Nov. 22, 2011

(54) METHOD AND SYSTEM FOR DETECTION OF BONE FRACTURES

(75) Inventors: Wee Kheng Leow, Singapore (SG); Dennis Yap, Singapore (SG); Tet Sen Howe, Singapore (SG); Meng Ai Png, Singapore (SG)

(73) Assignee: National University of Singapore, Singapore (SG)

( * ) Notice: Subject to any disclaimer, the term of this patent is extended or adjusted under 35 U.S.C. 154(b) by 1075 days.

(21) Appl. No.: 10/590,887

(22) PCT Filed: Feb. 28, 2005

(86) PCT No.: PCT/SG2005/000060
§ 371 (c)(1),
(2), (4) Date: Jul. 11, 2007

(87) PCT Pub. No.: WO2005/083635
PCT Pub. Date: Sep. 9, 2005

(65) Prior Publication Data
US 2007/0274584 A1    Nov. 29, 2007

Related U.S. Application Data

(60) Provisional application No. 60/548,836, filed on Feb. 27, 2004.

(51) Int. Cl.
*G06K 9/00* (2006.01)
(52) U.S. Cl. ........................................ 382/128
(58) Field of Classification Search .......... 382/128–134; 128/920–925; 356/39–49; 600/407–414, 600/424–426; 345/581–618
See application file for complete search history.

(56) References Cited

U.S. PATENT DOCUMENTS

| 5,776,063 | A | * | 7/1998 | Dittrich et al. | 600/408 |
| 2003/0215119 | A1 | * | 11/2003 | Uppaluri et al. | 382/128 |
| 2003/0215120 | A1 | | 11/2003 | Uppaluri et al. | |
| 2003/0223627 | A1 | * | 12/2003 | Yoshida et al. | 382/128 |
| 2005/0010106 | A1 | * | 1/2005 | Lang et al. | 600/425 |
| 2005/0111718 | A1 | * | 5/2005 | MacMahon et al. | 382/130 |

OTHER PUBLICATIONS

T.P. Tian et al., Computing Neck-Shaft Angle of Femur for X-Ray Fracture Detection Proc. Int. Conference on Computer Analysis of Images and Patterns, 2003, pp. 82-89.
T.P. Tian, Detection of Femur Fractures in X-Ray Images, as archived Jul. 2003.
S.E. Lim et al., Detection of Femur and Radius Fractures in X-Ray Images Proc. Int. Conf. On Advances in Medical Signal and Information Processing, Sep. 2004.
D.W. H. Yap et al., Detecting Femur Fractures by Texture Analysis of Trabeculae Proc. 17$^{th}$ International Conference on Pattern Recognition, vol. 3, Aug. 2004, pp. 730-733.
D.N. Davis et al., Diagnostic Classification of Leg Radiographs, May 2000.
M.M. Syiam et al., ADAGEN: Adaptive Interface Agent for X-Ray Fracture Detection Proc. Int. Conf. On Electrical, Electronic and Computer Engineering, Sep. 2004.
M.M. Syiam et al., PCA Neural Network for Extracting Features from Femur Fracture in X-Ray Images, CCIT 2004, Dec. 2004.
T.F. Cootes and A. Hill and C.J. Taylor and J. Haslam, The use of active shape models for locating structures in medical images, Image and Vision Computing, vol. 12, No. 6, 1994, pp. 355-366.

(Continued)

*Primary Examiner* — Samir Ahmed
*Assistant Examiner* — Atiba Fitzpatrick
(74) *Attorney, Agent, or Firm* — Knobbe Martens Olson & Bear LLP (57) ABSTRACT

A method and system for detection of bone fractures using image processing of a digitized x-ray image.

19 Claims, 9 Drawing Sheets

OTHER PUBLICATIONS

T.F. Cootes and G.J. Edwards and C.J. Taylor, Active Appearance Models, Proceedings of European Conference on Computer Vision, 1998.

P.J. Besl and N.D. McKay, A method for registration of 3-D shapes, IEEE Transactions on Pattern Analysis and Machine Intelligence, vol. 14, No. 2, 1992, pp. 239-256.

M. Kass and A. Witkin and D. Terzopoulos, Snakes: Active Contour Models, International Journal of Computer Vision, vol. 1, 1987, pp. 321-331.

C. Cortes and V. Vapnik, Support vector networks, Machine Learning, vol. 20, 1995, pp. 273-297.

A.C. Bovik and M. Clark and W.S. Geisler, Multichannel texture analysis using localized spatial filters, IEEE Transactions on Pattern Analysis and Machine Intelligence, vol. 12, No. 1, 1990, pp. 55-73.

G.R. Cross and A.K. Jain, Markov random field texture models, IEEE Transactions on pattern Analysis and Machine Intelligence, vol. 5, 1983, pp. 25-39.

* cited by examiner

|  | NSA | Gabor | | IGD | | MRF | Combined | | | |
|---|---|---|---|---|---|---|---|---|---|---|
|  |  | Bayes | SVM | Bayes | SVM | SVM | 1 of 5 | 1 of 6 | 2 of 6 | 2 of 4 |
| fracture detection rate | 61.5% | 53.9% | 69.2% | 38.5% | 53.9% | 14.3% | 100% | 100% | 92.2% | 76.9% |
| false alarm rate | 1.9% | 0.0% | 2.9% | 4.8% | 1.0% | 1.8% | 10.5% | 11.4% | 1.0% | 0.0% |
| classification accuracy | 93.5% | 94.4% | 93.5% | 88.0% | 93.5% | 89.5% | 89.8% | 88.9% | 98.2% | 97.2% |

| | left | right | overall |
|---|---|---|---|
| fracture detection rate | 80.0% | 84.6% | 82.6% |
| false alarm rate | 15.2% | 19.5% | 17.6% |
| classification accuracy | 78.8% | 75.6% | 77.0% |

METHOD AND SYSTEM FOR DETECTION OF BONE FRACTURES

RELATED APPLICATIONS

This application claims priority under 35 U.S.C. §119(e) from U.S. Provisional Application No. 60/548,836 filed Feb. 27, 2004, which is hereby incorporated by reference.

FIELD

This invention relates to automated screening and detection of bone fractures in x-ray images.

BACKGROUND

Many people suffer from fractures of the bone, particularly elderly people. According to the findings of the International Osteoporosis Foundation, the lifetime risk for osteoporotic fractures in women is 30%-40% worldwide, and 13% in men. The number of hip fractures could rise from 1.7 million worldwide in 1990 to 6.3 million by 2050. Most dramatic increase is expected to occur in Asia during the next few decades. According to World Health Organization, osteoporosis is second only to cardiovascular disease as a leading health care problem.

In clinical practice, doctors and radiologists in large hospitals rely mainly on x-ray images to determine the occurrence and the precise nature of the fractures. Visual inspection of x-rays for fractures is a tedious and time-consuming process. Typically, the number of images containing fractures constitutes a small percentage of the total number of images that the radiologists have to inspect. For example, in a sample of x-ray images of femurs collected, only about 10% of them are fractured. After looking through many images containing healthy femurs, a tired radiologist has been found to miss a fractured case among the many healthy ones.

Some methods of bone fracture detection utilize non-visual techniques to detect fractures. This includes using acoustic pulses, mechanical vibration and electrical conductivity.

Furthermore, existing methods of bone fracture detection mostly fail to consider that the shapes and sizes of the bones are not identical. Even among healthy bones, there are still differences in the appearance because they are naturally-occurring objects. Age and gender also contribute to the difference in the appearance of the bones. One standard method of dealing with size variation is to normalize the size of the bones in the captured x-ray images for visual inspection. This method is, however, unsatisfactory because it can either remove important texture information (if the image is shrunken) or introduce noise and artifacts (if the image is enlarged).

SUMMARY

In accordance with a first aspect of the present invention there is provided a method for detection of bone fractures using image processing of a digitized x-ray image.

The image processing may comprise extracting a contour of the bone in the digitized x-ray image.

The extracting of the contour of the bone in the digitized x-ray image may comprise applying a Canny edge detector to the digitized x-ray image.

The extracting of the contour of the bone in the digitized x-ray image may comprise applying a snake algorithm to the digitized x-ray image.

Applying the snake algorithm to the digitized x-ray image may comprise creating a Gradient Vector Flow (GVF).

The image processing may comprise an adaptive sampling scheme.

The adaptive sampling scheme may comprise identifying a bounding box around an area of interest based on the extracted contour of the bone.

The bounding box may be divided into a predetermined number of sampling points.

A sampling region around the sampling points may be chosen to cover image pixel points between the sampling points.

The image processing may comprise calculating one or more texture maps of the digitized x-ray image and detecting a bone fracture based on respective reference texture maps.

The texture maps may comprise a Gabor texture orientation map.

The texture maps may comprise a Intensity gradient direction map.

The texture maps may comprise a Markov Random Field texture map.

The image processing may comprise calculating one or more difference maps between the respective texture maps calculated for the digitized x-ray image and the respective reference texture maps.

The difference maps may be classified using one or more classifiers.

The difference maps may be classified using Bayesian classifiers.

The difference maps may be classified using Support Vector Machine classifiers.

The image processing may comprise determining a femoral shaft axis in the digitized x-ray image; determining a femoral neck axis in the digitized x-ray image; measuring an obtuse angle between the femoral neck axis and the femoral shaft axis; and detecting the bone fracture based on the measured obtuse angle.

The method may further comprise calculating level lines from respective points on the contour of the bone in the digitized x-ray image and extending normally to the contour to respective other points on the extracted contour.

Determining the femoral shaft axis may be based on midpoints of the level lines in a shaft portion of the contour of the bone.

Determining the femoral neck axis may be based on the level lines in femoral head and neck portion of the contour of the bone.

In accordance with a second aspect of the present invention there is provided a system for detection of bone fractures comprising means for receiving a digitized x-ray image; and means for processing the digitized x-ray image for detection of bone fractures.

In accordance with a third aspect of the present invention there is provided a system for detection of bone fractures comprising a database for receiving and storing a digitized x-ray image; and a processor for processing the digitized x-ray image for detection of bone fractures.

BRIEF DESCRIPTION OF THE DRAWINGS

The accompanying drawings, which are incorporated into and constitute a part of the description of the invention, illustrate embodiments of the invention and serve to explain the principles of the invention. It is to be understood, however, that the drawings are designed for purposes of illustration

DETAILED DESCRIPTION

For illustration, the example embodiments of the present invention will be described by the detection of femur fractures, as they are the most common types of fractures. Some preliminary results on the detection of fractures of the radius near the wrist will also be discussed.

An example embodiment of the present invention provides a computer system and method for automated screening and detection of bone fractures in digital x-ray images. The system can analyze digital x-ray images of the bones and perform the following tasks:

Determine whether the bones are healthy or fractured, and compute confidence of the assessment;

Identify cases suspected of fractures and highlight the possible areas where fractures may have occurred.

The steps involved are:

1. Read digital x-ray images stored in an external storage device.
2. Identify the regions of the images where the bones of interests are located.
3. Determine whether the bones of interests are fractured, and measure the confidence of the assessment.
4. Mark the locations where fractures are suspected for images that contain possibly fractured bones.
5. Display on an output device the results of the automated analysis, including but not limited to
    whether the bones of interests are fractured, and the associated confidence;
    the locations of suspected fractures; and
    alerting the doctors to the suspected fractures.

The method utilised in the example embodiment will be described in detail as follow. The system utilised by the example embodiment will be discussed in the later part of this description.

The example embodiment of the present invention adopts an approach in detecting fractures of the femur and the radius by combining different detection methods. These methods extract different kinds of features for fracture detection. They include neck-shaft angle, which is specifically extracted for femur fracture detection, and Gabor texture, Markov Random Field texture, and intensity gradient, which are general features that can be applied to detecting fractures of various bones. Two types of classifiers are utilised, namely, Bayesian classifier and Support Vector Machine.

The method of detecting fractures in the example embodiment can be divided into 3 stages: (1) extraction of approximate contour of the bone of interest in the x-ray image, (2) extraction of features from the x-ray image, and (3) classification of the bone based on the extracted features.

In the example embodiment, the extraction of bone contour in stage 1 is performed using an active shape model, supplemented by active appearance models at distinct feature points.

In more detail, the process of identifying or extraction of the bone contour (i.e. the locations of the bones of interests) consists of applying (1) the Active Shape Model to determine the initial prediction of the outer contour of the bones, (2) the Active Appearance Model to determine accurately landmark locations along the initial prediction of the bone contour and followed by (3) refinement of the bone contour to determine the exact contour of the bone.

In the example embodiment of the present invention, the refinement of the bone contour is performed using an Iterative Closest Point method. Alternatively, the refinement of the bone contour can be performed using an Active Contour (i.e., Snake) method.

In stage 2, the process of fracture detection after the locations of the bone of interest are identified consists of a combination of methods. Each method is based on the extraction of a particular image feature and each method examines fracture based on different aspects of the x-ray image.

In the example embodiment, four different types of image features are extracted for fracture detection: (1) femoral neck-shaft angle, (2) Gabor texture, (3) Markov Random Field (MRF), and (4) intensity gradient. The first feature is specifically extracted for detecting the distortion of shape due to severe femur fracture. The other features are applied to detect fractures of various bones or different types of fractures, for example, MRF is typically utilised for detecting radius fractures.

The methods for extracting the four different types of image features are described in detail as follow.

Figure 1:
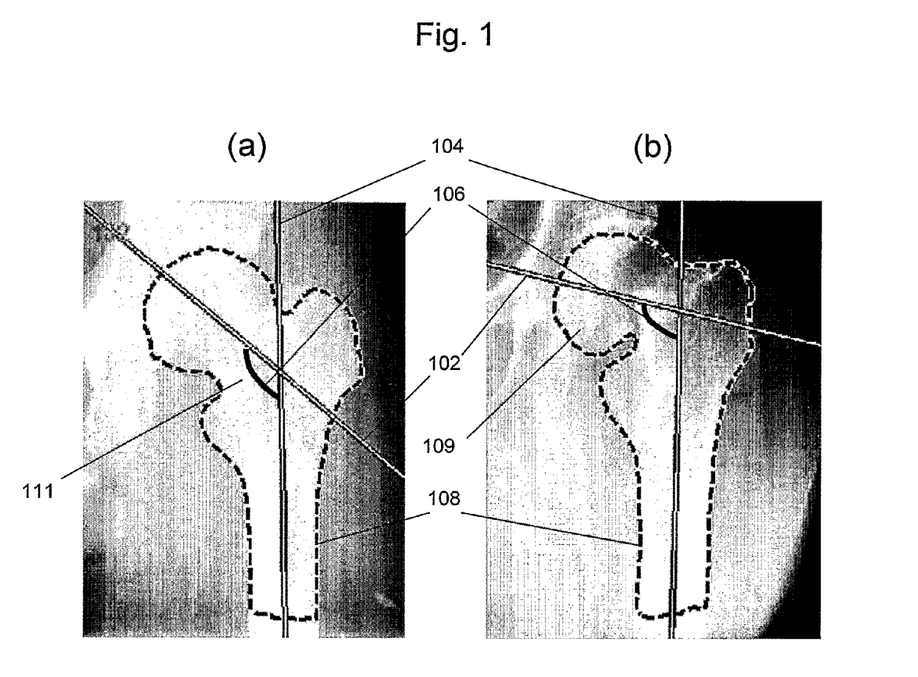
FIG. 1a shows an x-ray image of a healthy femur with a normal neck-shaft angle illustrating processing of a digitized x-ray image according to an example embodiment.
FIG. 1b shows an x-ray image of a fractured femur with a smaller-than-normal neck-shaft angle illustrating processing of a digitized x-ray image according to an example embodiment.

The first method is based on measuring the femoral neck-shaft angle. With reference to FIGS. 1a and 1b, the method comprises (1) determining the femoral neck axis 102, (2) determining the femoral shaft axis 104, and (3) measuring the obtuse angle 106 made by the neck axis and the shaft axis. Images with neck-shaft angle 106 smaller than a pre-specified angle are flagged as suspected fractured cases. For example, assuming the pre-specified neck-shaft angle 106 of a healthy femur is as shown in FIG. 1a, FIG. 1b shows the case of a bone fracture with neck-shaft angle 106 smaller than the pre-specified angle. The difference between the measured angle and the pre-specified angle is regarded as a measure of the confidence of the assessment.

The algorithm for extracting the contour of the femur in the example embodiment consists of a sequence of processes. First a modified Canny edge detector is used to compute the edges from the input x-ray image of the hip followed by computing a Gradient Vector Flow field for the edges. Next, a snake algorithm combined with the Gradient Vector Flow will move the active contour, i.e., the snake, to the contour of the femur.

In more detail, the Canny edge detector takes as input a gray scale image and produces as output an image showing the position of the edges. The image is first smoothed by Gaussian convolution. Next, a simple 2D first derivative operator is applied to the smoothed image to highlight regions of the image with high first derivatives. Using the gradient direction calculated, the algorithm performs non-maxima suppression to eliminate pixels whose gradient magnitude is lower than its two neighbors along the gradient direction. Finally these thin edges are linked up using a technique involving double thresholding. Although Canny edge detector works well in detecting the outline of the femur, it may also detects a large number of spurious edges close to the shaft. Such spurious edges may affect the snake's convergence on the outline of the femur and are preferably removed. Attempting to remove the spurious edges by increasing the smoothing effect will reduce these spurious edges but the edge information at the femur head may also be lost. Contributing to the problem is the fact that the femur head overlaps with the hip bones and edge magnitudes of the femur head in this region are low.

The problem of preserving femur head edges and at the same time removing spurious edges can be solved by incorporating information from the intensity image into the Canny edge algorithm in the example embodiment. It was found that areas containing bones have higher intensity than non-bone regions. Hence this information can be used to distinguish spurious edges from femur head edges. The Canny edge detector with a small smoothing effect is used to detect the femur head edges while spurious edges with both low intensity value and low gradient magnitude values are removed.

In summary, a pixel is marked as an non-edge point in the example embodiment if
1) it is detected by Canny edge detector,
2) it has an intensity lower than a threshold I', and
3) it has an edge magnitude lower than the same threshold I'.

The threshold I' is a percentage value. In the example embodiment, a non-edge pixel must have an intensity and an edge magnitude lower than 90% of the total pixels.

In example embodiment makes use of a snake to snap onto the contour of the femur snakes are formulated as energy-minimizing contours controlled by two forces:
1) Internal contour forces which enforce the smoothness constraint.
2) Image forces which attracts the contour to the desired features, in this case, edges $$E_{snake} = \int_j^1 E_{int}(v(s)) + E_{image}(v(s)) ds$$

Representing the position of the snake parametrically by $v(s) = (x(s), y(s))$, the energy of a snake $E_{snake}$ is a sum of the internal energy $E_{int}$ of the snake and the image energy $E_{image}$.

A snake that minimize the energy functional $E_{snake}$ must satisfy the following Euler equations:

$$\alpha x_{ss} + \beta x_{ssss} + \frac{\partial E_{image}}{\partial x} = 0$$

$$\alpha y_{ss} + \beta y_{ssss} + \frac{\partial E_{image}}{\partial y} = 0$$

Where $x_{SS}$ and $x_{SSSS}$ are the second and fourth derivatives of x, similarly for $y_{SS}$ and $y_{SSSS}$.

In the example embodiment, a gradient Vector Flow (GVF) was created to improve the original active contour formulation. GVF is computed as a diffusion of the gradient vectors of a gray-level edge map derived from the image.

The GVF field is defined as the vector field $G(x, y) = (q(x, y), r(x, y))$ that minimizes the energy functional $$\epsilon = \iint \mu(q_x^2 + q_y^2 + r_x^2 + r_y^2) + |\nabla E|^2 |G - \nabla E|^2 dx dy$$

where E is an edge map $E(x, y)$ derived from the image. Using calculus of variations, the GVF can be found by solving the following Euler equations $$\mu \nabla^2 q - (q - E_x^2 - E_y^2) = 0$$

$$\mu \nabla^2 r - (r - E_x^2 - E_y^2) = 0$$

The snake algorithm is combined with the external force computed by the GVF to improve the performance of snake. With the GVF snake, in the example embodiment, only a small number of initialization points are needed to start the snake algorithm and successive iterations of the algorithm will redistribute the snake points more regularly along the contours.

In the computation of femoral neck-shaft angle 106, lines that are normal to both sides of the shaft contour, which are called the level lines, are computed from the contour of the femur 108. The construction of the level lines is based on the normals of the contour points. There are a number of ways to compute the normal for a point on the contour 108. In the example embodiment, finite difference to estimate the derivative and hence derive the normal direction is used. This technique uses a small number of points in the neighborhood of the point of interest to derive the normal. It is sensitive to small changes in the neighbors' positions of the points.

In another embodiment, with a dense sampling of points along the contour, a larger set of points can be used to compute the normal at a point using Principal Component Analysis (PCA). To compute the normal of a contour point, choose a neighborhood of points around the point of interest. This set of points represents a segment of the contour and PCA is applied to this segment of points. Given a set of points in 2D, PCA returns two eigenvectors and their associated eigenvalues. The eigenvector with the largest eigenvalue will point in the direction parallel to this segment of points and the other eigenvector gives the normal direction at the point of interest.

Once the normal for each point on the contour has been calculated, the set of level lines L can be computed. The orientation of the femur shaft can be computed by extracting the mid-points of the level lines on the shaft area of the contour 108. After finding the midpoints of the shaft, the PCA algorithm is used to estimate the orientation of the midpoints in the example embodiment. The eigenvector with the largest eigenvalue computed from the PCA algorithm will represent the orientation of the shaft midpoints.

The computation of femoral neck's orientation is more complicated because there is no obvious axis of symmetry. The algorithm in the example embodiment consists of three main steps. 1) compute an initial estimate of the neck orientation, 2) smooth the femur contour, and 3) search for the best axis of symmetry using the initial neck orientation estimate.

The longest level lines in the upper region of the femur always cut through the contour of the femoral head 109. Given this observation, an adaptive clustering algorithm is used in the example embodiment to cluster long level lines at the femoral head 109 into bundles of closely spaced level lines with similar orientations. The bundle with the largest number of lines is chosen, and the average orientation of the level lines in this bundle is regarded as the initial estimate of the orientation of the femoral neck.

The adaptive clustering algorithm is useful as it does not need to choose the number of clusters before hand. The general idea is to group the level lines such that in each group, the level lines are similar in terms of orientation and spatial position. The adaptive clustering algorithm groups a level line into its nearest cluster if the orientation and midpoint of the cluster is close. If a level line is far enough from any of the existing clusters, a new cluster will be created for this level line. For level lines that are neither close nor far enough, they will be left alone and not assigned to any cluster. With the adaptive clustering algorithm, it ensures each cluster has a minimum similarity of R1 for the cluster orientation and minimum similarity of R2 for the mid-points distance. The algorithm also ensures that the cluster differs by a similarity of at least S1 and S2 for the orientation and mid-points distance respectively.

Varying the values of R1, R2, S1 and S2 controls the granularity of clustering and the amount of overlapping between clusters. The general idea of determining the axis of symmetry is to find a line through the femoral neck 111 and head 109 such that the contour of the head and neck coincides with its own reflection about that line. Given a point $p_k$ along the contour of the femoral head and neck, obtain the midpoint $m_i$ along the line joining contour point $p_{k-i}$ and $p_{k+i}$. That is, one obtains a midpoint for each pair of contour points on the opposite sides of $p_k$. Now, one can fit a line $I_k$ through the midpoints $m_i$ to obtain a candidate axis of symmetry. If the contour is perfectly symmetrical, and the correct axis of symmetry is obtained, then each contour point $p_{k-i}$ is exactly the mirror reflection of $p_{k+i}$. The best fitting axis of symmetry is a midpoint fitting line $I_t$ that minimizes the error.

The best fitting axis of symmetry is determined to obtain the best approximation of the neck axis 102. Finally, the obtuse angle 106 between the neck and the shaft axes can be computed. Classification of whether the bone is healthy or not is based on a threshold of the neck-shaft angle 106 that is learned from training samples.

In the example embodiment, the methods for extracting the other three image features, Gabor texture, Markov Random Field (MRF) and intensity gradient, share a common trait: adaptive sampling. As such, before the other methods are discussed in detail, adaptive sampling will be discussed.

As discussed earlier, shapes and sizes of the bones are not identical in the x-ray images, even among healthy bones. The standard method of dealing with size variation in computer vision is to normalize the size of the bones in the images. However, normalizing may cause important texture information to be removed (if the image is shrunken) and introduce noise and artifacts (if the image is enlarged). The example embodiment prevents this from happening by using adaptive sampling to sample the features so that the sampled locations in different images correspond to consistent locations in the normalized sampling grid instead of scaling the x-ray images.

Figure 2:
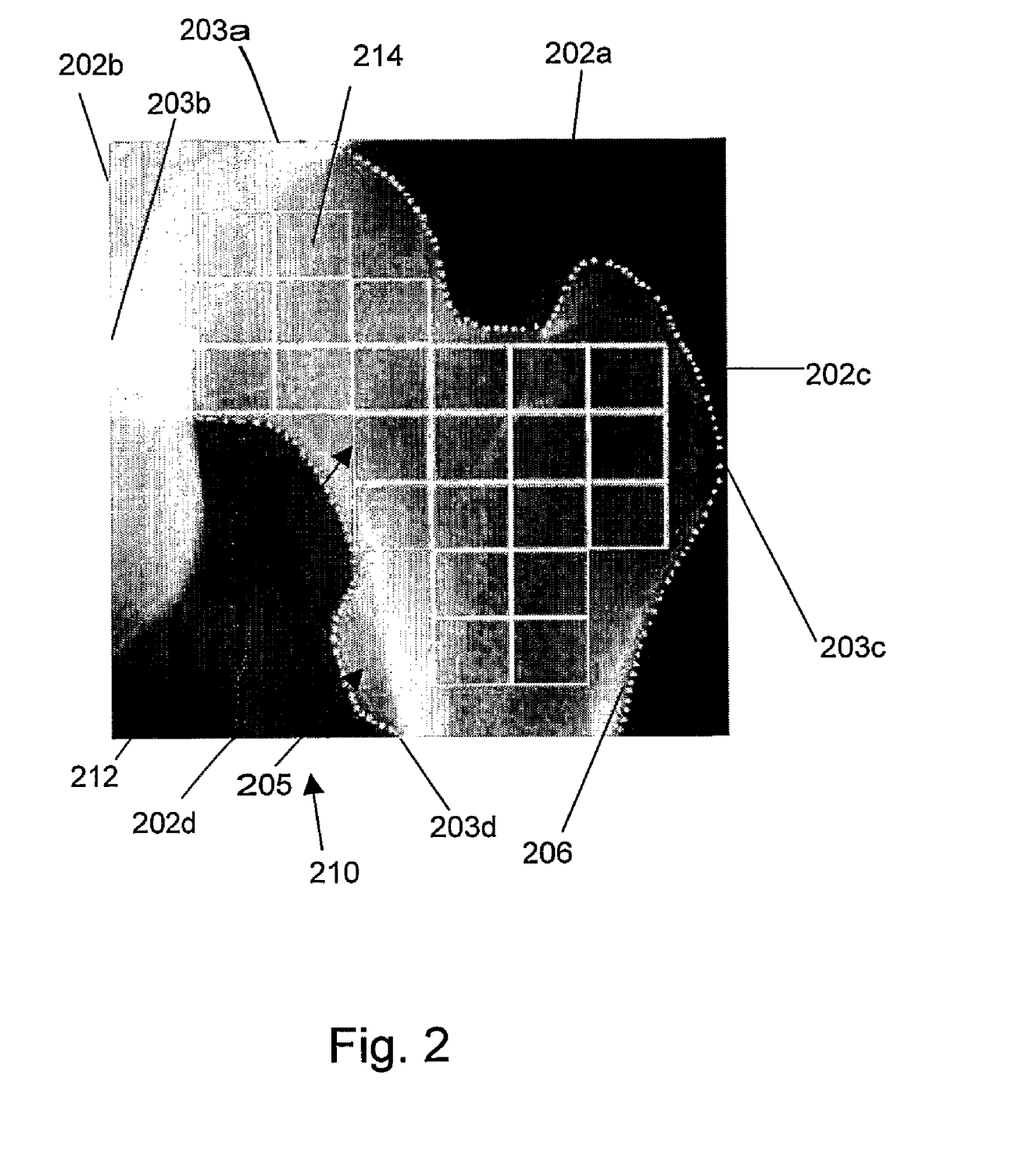
FIG. 2 shows an adaptive sampling grid utilised in an example embodiment of the present invention.

Let W and H denote the width and height of a bounding box 202 that contains the bone of interest, e.g. the femur's upper extremity, as shown in FIGS. 2a and b. This bounding box 202 is automatically derived from the approximate bone contour extracted in stage 1 (extraction of bone contour) of the algorithm In the example embodiment, the upper bounding box side 202a is determined by a horizontal line through the uppermost point 203a on the bone contour 206. One left and right sides 202b, c respectively of the bounding box 202 are determined based on the vertical lines through the left- and rightmost points 203b, c respectively on the bone contour 206 the lower bounding box side 202d is determined by a horizontal line through the lowest point 203d of the lesser tronchanter 205 on the bone contour 206.

Let $n_x$ and $n_y$ denote the number of sampling locations along the x- and y-directions, which means the sampling method divides the whole bounding box into $n_x \times n_y$ regions, with $n_x <$ number of horizontal image pixels, and $n_y <$ number of vertical image pixels in the example embodiment. As a result of utilizing adaptive sampling, the example embodiment needs to extract only approximate bone contours. Therefore, slight variation of shape over different patients can be tolerated.

FIG. 2 shows a grid 212 of sampling points e.g. 214 inside the bounding box 202 which fall inside the bone contour 206. In the example embodiment, the features are extracted from each sampling region around a sampling point that is determined using the adaptive sampling method. The number of sampling points differ for different feature types. For example, texture features extracted using Gabor filtering requires a larger sampling region and thus fewer sampling points. On the other hand, e.g. extraction of intensity gradient requires smaller sampling region, thus sampling can be performed at more sampling points. Markov Random Field (MRF) texture model extracts features from medium-sized sampling regions compared with the larger sampling regions for Gabor filtering and the smaller sampling regions for intensity gradient extraction.

In the following, the methods of extracting image features using Gabor filters, Markov Random Field (MRF) and intensity gradient respectively will be described in more detail.

Generally, in the example embodiment, each of the methods of extracting the three features will first generate a feature map, which will be later used during classification to detect whether an x-ray image shows a healthy bone or a fractured bone. The feature map is a record of the visual features at various locations of the femur image.

After the feature maps are generated, a mean feature map is computed by averaging the maps of sample healthy femur images. To determine whether a fracture exists, the difference between the feature map of an input femur image and the mean feature map is performed to produce a difference map. Then, during classification, the difference map is classified through Bayesian math or Support Vector Machine (SVM) to determine whether a fracture exists. In SVM, the distance between the difference map and the hyperplane computed by the SVM is regarded as a measure of the confidence of the assessment.

One principle for fracture detection is that the trabeculae in bones are oriented at specific orientations to support the forces acting on them. Therefore, a fracture of the bone causes a disruption of the trabecular pattern, which can be detected by extracting various feature types.

Figure 3:
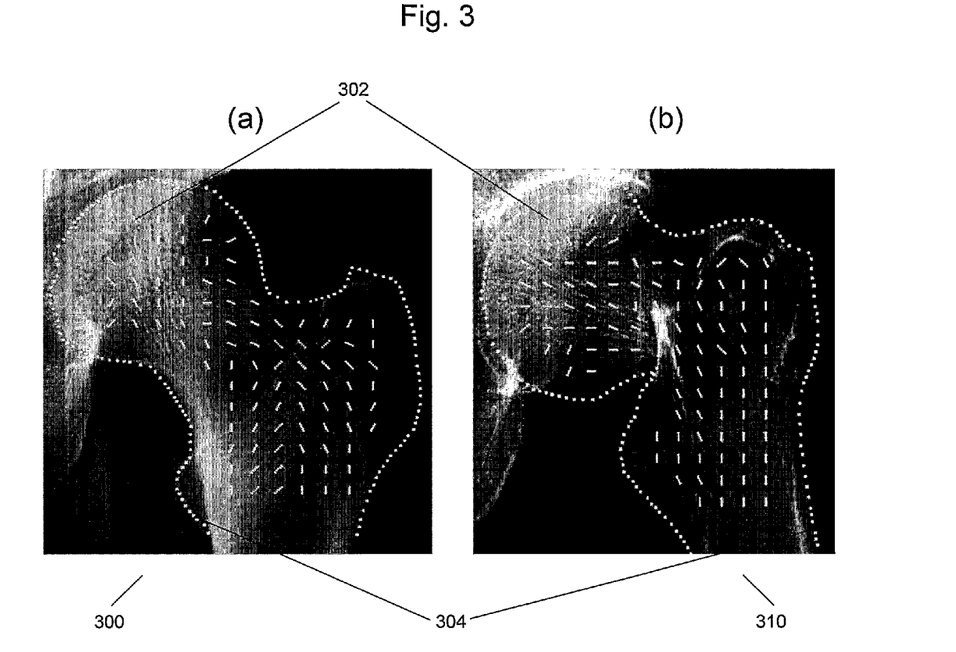
FIG. 3a shows the Gabor texture orientation map of a healthy femur illustrating processing of a digitized x-ray image according to an example embodiment.
FIG. 3b shows the Gabor texture orientation map of a fractured femur illustrating processing of a digitized x-ray image according to an example embodiment.

In the example embodiment, by extraction of Gabor textures, the result is a Gabor texture orientation map $M_G=[u_{ij}]$ where $u_{ij}$ is a unit vector that represents the Gabor texture orientation at 2 Dimension grid location (i,j). The Gabor texture orientation map records the orientations of the trabecular lines at various locations in the femur image. The orientations are computed by filtering the image with a set of Gabor filters with different orientation preferences. At each location, the orientation of the Gabor filter with the largest response indicates the orientation of the trabecular lines at that location. FIGS. 3a and 3b illustrate examples of Gabor texture orientation maps generated based on Gabor filtering. FIG. 3a shows the texture orientation map of a healthy femur 300 and FIG. 3b shows the texture orientation map of a fractured femur 310. The short lines 302 plotted within the bone contour regions 304 indicate the trabecular orientations.

Before extracting the intensity gradient feature in the example embodiment, the x-ray images are normalized first so that their mean intensities and contrasts are similar. This is followed by computing the intensity gradient.

One way of computing the intensity gradient at a point p is to fit a curve surface on the intensity profile at and around p. Then, the intensity gradient is computed by applying analytical geometry.

Another way, which is utilised in the example embodiment, is to apply an approximation method as follows.

Given a region R(p) centered at p, search within the region for a point q whose intensity difference $d_m$ is the largest:

$$d_m(p) = \max_{q' \in R(p)} |I(p) - I(q')|$$

where I(p) and I(q') denote Intensity at p and Intensity at arbitrary point q' within R(p) respectively.

Figure 4:
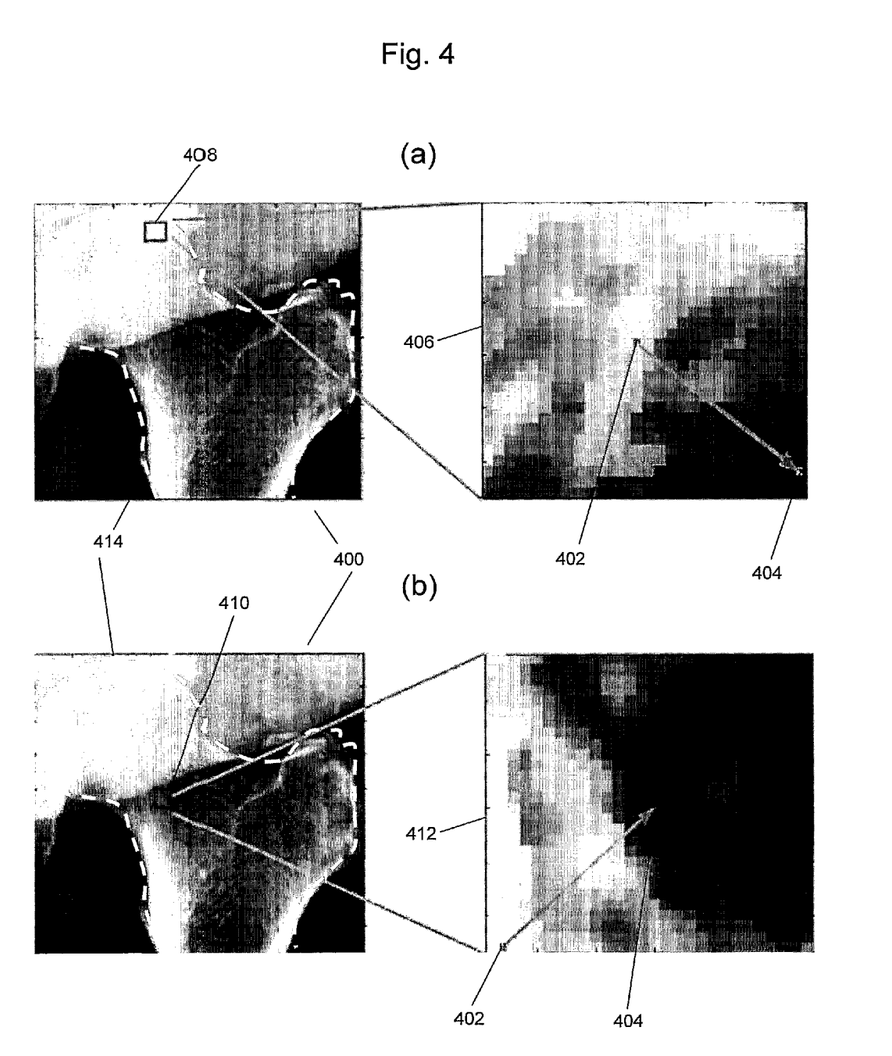
FIG. 4a shows the intensity gradient direction at one location of an x-ray image of a human femur illustrating processing of a digitized x-ray image according to an example embodiment.
FIG. 4b shows the intensity gradient direction at another location of the x-ray image of a human femur illustrating processing of a digitized x-ray image according to an example embodiment.

Then, the intensity gradient direction g(p) is computed as the vector difference $$g(p) = \text{sgn}(I(p) - I(q)) \frac{q - p}{d_m(p)}$$

where sgn(.) is the sign function. As shown in FIGS. 4a and 4b, the direction of g is defined to point from higher intensity location (brighter region) 402 to lower intensity location (darker region) 404 as shown in two sample zoom-in images (406 and 412) at different locations (408 and 410) of the same x-ray image 400. Next, Intensity gradient direction can be computed at each location (i,j) within the bone contour 414 to form the intensity gradient direction map $M_g=[u_{ij}]$. Gradient direction outside the contour 414 is defined to be the null vector.

Figure 5:
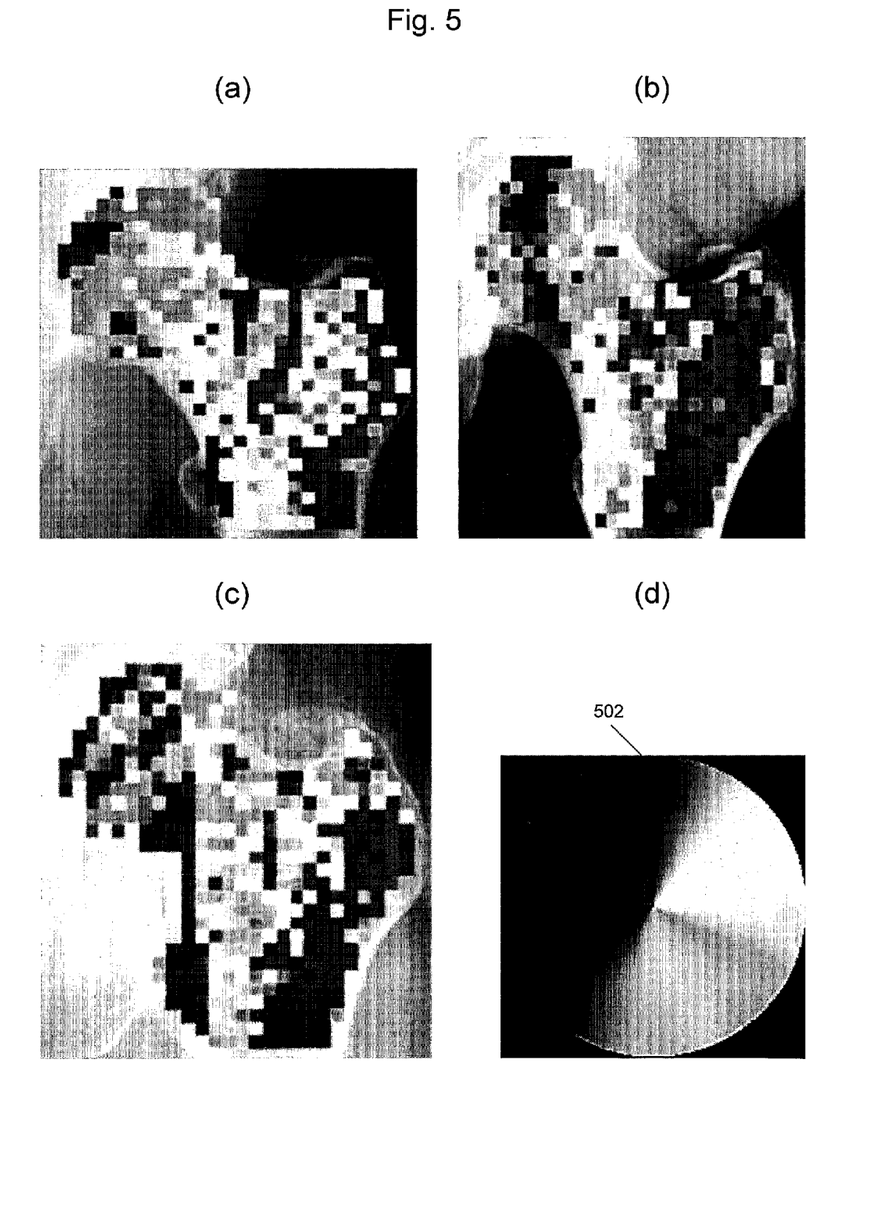
FIG. 5a shows the intensity gradient direction map of a healthy femur in an x-ray image illustrating processing of a digitized x-ray image according to an example embodiment.
FIG. 5b shows the intensity gradient direction map of another healthy femur in an x-ray image illustrating processing of a digitized x-ray image according to an example embodiment.
FIG. 5c shows the intensity gradient direction map a fractured human femur illustrating processing of a digitized x-ray image according to an example embodiment.
FIG. 5d shows a shaded circle, which is the reference for intensity gradient directions illustrating processing of a digitized x-ray image according to an example embodiment.

FIGS. 5a, 5b and 5c illustrate examples of intensity gradient direction maps. FIGS. 5a and 5b show two different x-ray images of healthy femurs and FIG. 5c shows a fractured femur. The directions of each location in the intensity gradient direction maps is represented by different shades of black, white and gray as depicted in the 2 Dimensional diagram of a 3 Dimensional shaded circle 502 in FIG. 5d.

Similar to the extraction of intensity gradient feature, intensity normalization is also performed in the example embodiment before extracting the Markov Random Field texture. The Markov Random Field texture model describes the intensity of a pixel p as a linear combination of those of its neighbors q:

$$I(p) = \sum_{q \in R(p)} (\theta(p,q)I(p+q) + \epsilon(q))$$

where $\theta(p,q)$ are model parameters and $\epsilon(q)$ represents noise, which is usually assumed to be Gaussian noise of zero mean and constant variance. The model parameters $\theta(p,q)$ at location p is then computed by minimizing the error E:

$$E = \left[ I(p) - \sum_{q \in R(p)} (\theta(p,q)I(p+q) + \epsilon(q)) \right]^2$$

The model parameters $\theta(p,q)$ are then normalized to unit vectors $u_{ij}$ to form the MRF texture map $M_m=[u_{ij}]$, where p=(i,j). As for the other feature maps, entries outside the bone contour are assigned the null vectors.

The three feature maps Gabor texture orientation map, intensity gradient direction map and MRF texture map discussed above are vector maps and thus not typically convenient for classification of bones into classes of description such as fractured bones, healthy bones, suspected fracture, faulty image . . . etc. Therefore, in the example embodiment, they are first converted into difference maps, which are scalar maps, before classification For each feature type, the mean feature map of all the healthy training samples of x-ray femur images, $\overline{M}=[m_{ij}]$, is first computed. The entry $m_{ij}$ is the mean feature vector at position (i,j) in $\overline{M}$ and it is given by:

$$m_{ij} = \begin{cases} \sum_{k=1}^{n} u_{kij} \left\| \sum_{k=1}^{n} u_{kij} \right\|^{-1} & \text{if } c_{ij} > n/2 \\ 0 & \text{otherwise} \end{cases}$$

where n is the number of training samples, $u_{kij}$ is the unit feature vector of sample k at position (i,j), and $c_{ij}$ is the number of samples with non-null feature vectors at position (i,j).

Furthermore, in the generation of the mean feature map, for a particular position (i,j), if more than half of the training samples' feature maps have null values at this position, it will be considered as an insignificant position, which means this position does not contain significant information for classification. Then, the corresponding entry in the mean feature map will be assigned the null vector 0. This situation usually occurs near the boundary contour of the bone because of slight shape variation among different images. By setting the map entries at these positions to 0, the effect of slight shape variations on classification can be removed.

Now, the difference map $V=[v_{ij}]$ for all the training samples can be computed. Each entry $v_{ij}$ indicates the difference between the image's feature map and the mean feature map at the same position (i,j). $v_{ij}$ is governed by:

$$v_{ij} = \begin{cases} 0 & \text{if } u_{ij} = m_{ij} = 0 \\ 1 - |u_{ij} \cdot m_{ij}| & \text{otherwise} \end{cases}$$

A $v_{ij}$ value that is close to 0 indicates a slight difference between the image's feature map and the mean feature map at the same position (i,j), and a large $v_{ij}$ would indicate a large difference. As the mean feature map is computed over a collection of different healthy training samples, a randomly selected image of a healthy bone should have a feature map that is very similar to the mean feature map. Therefore, the difference map of the randomly selected image of a healthy bone is expected to have mostly small values. On the other hand, in an image of a fractured bone, there will be some disruption of the trabecular pattern caused by the fracture. So its feature map will be very different from the mean feature map at some positions, thus its difference map is expected to have some large values.

In the next stage, classification of bones for an x-ray image will be performed based on the values of the difference map. In the example embodiment, at the step of classification, two classifiers are applied on the difference maps to classify the test samples, 1) Bayesian and 2) Support Vector Machine (SVM).

For the Bayesian method, the sets of healthy and fracture training samples' difference maps are each modeled by a multivariate Gaussian function, which are used to estimate the conditional probabilities P(x|healthy) and P(x|fracture), where x denotes a sample's difference map. It was found that, in practice, the a priori probabilities P(healthy) and P(fracture) are not identical. For example, P(healthy) is roughly 0.88 and P(fracture) is 0.12 for the femur images in our collection. Applying Bayes' rule, we obtain $$P(\text{class} \mid x) = \frac{P(x \mid \text{class})P(\text{class})}{P(x)}$$

where class is either healthy or fractured. The denominator P(x) is the same for both P(healthy|x) and P(fracture|x) and so can be ignored. Thus, sample x can be classified as fractured if P(healthy|x) is smaller than P(fracture|x).

For the second method, Support Vector Machine is used for classification. The objective of SVM can be stated succinctly as follow:

Given the training set $\{(x_i, d_i)\}_{i=1}^{n}$, where $d_i$ is the class of feature vector $x_i$, find the optimal hyperplane, in terms of weights w and bias b, that satisfies $$d_i(w^T x_i + b) \geq 1 \text{ for } i=1, \ldots, n$$

and minimizes $\Phi(w) = w^T w/2$.

The optimal weights w are given by a set of Lagrange multipliers $\alpha_i$:

$$w = \sum_i \alpha_i d_i x_i$$

The training vectors $x_i$ with non-zero $\alpha_i$ are the support vectors.

For practical applications, which are typically nonlinearly separable, the example embodiment solves the classification problem in a high-dimensional space where there is a better chance of achieving linear separation. This is accomplished by applying a nonlinear function $\phi(x)$ to map the vector x in an n-dimensional input space to an m-dimensional feature space, m>n. Then, the optimal hyperplane in the m-dimensional feature space is given by:

$$w^T \phi(x) + b = 0$$

The nonlinear function $\phi(x)$ is a kernel function of the form $K_i(x) = K(x, x_i)$ where $x_i$ are the support vectors. Then, the optimal hyperplane in the feature space becomes:

$$\sum_i \alpha_i d_i K(x, x_i) + b = 0$$

And the decision function f(x) becomes $$f(x) = \sum_i \alpha_i d_i K(x, x_i) + b$$

For efficient computation, the kernel functions must satisfy the so-called Mercer's Theorem. These kernel functions include:
1. Polynomial:

$$K(x, xi) = (x^T x_i + 1)^p$$

where p is a constant.
2. Gaussian or Radial Basis Function:

$$K(x, xi) = \exp\left(-\frac{\|x - x_i\|^2}{n\sigma^2}\right)$$

where $\sigma$ is the standard deviation of the Gaussian and n is the number of training samples.
3. Hyperbolic Tangent:

$$K(x, xi) = \tan h(\beta_0 x^T x_i + \beta_1)$$

where $\beta_0$ and $\beta_1$ are constants and noting that Mercer's theorem is satisfied only for some values of $\beta_0$ and $\beta_1$.

The following describes the experiments and results of a practical implementation of an example embodiment of the present invention for bone fracture detection. In the practical implementation of the example embodiment, the number of sampling locations for the adaptive sampling method was set as shown in table 1 below,

TABLE 1

|  | Gabor | IG | MRF (femur) | MRF (radius) |
|---|---|---|---|---|
| $n_x$ | 12 | 28 | 16 | 8 |
| $n_y$ | 14 | 32 | 24 | 15 | where MRF: Markov Random Field model, IG: intensity gradient and Gabor and IG were extracted only from femur images. Recall that $n_x$ and $n_y$ denotes the number of sampling locations along the x- and y-directions and there exists $n_x \times n_y$ regions in the bounding box containing the bone of interest.

For classification, optimal values of the Radial Basis Function (RBF) parameter and weighting factors were determined by experimentation on the training samples. The RBF with parameter σ=2 was chosen as the kernel function because RBF kernel yields better classification results. Furthermore, different weighting factors were assigned to the errors associated with the training samples, as this was useful for encoding different significant levels of the training samples, and for handling imbalanced number of positive and negative training samples. The weighting factor of the healthy femurs was set as 15 and that of the fractured femurs was set as 100. The weighting factor of the fractured femurs was purposely set to a higher value because in a typical practical situation there were much fewer fractured samples than healthy samples.

In one experiment, 432 femur images were obtained from a local public hospital, and were divided randomly into 324 training and 108 testing images. The percentage of fractured images in the training and testing sets were kept approximately the same (12%). In the training set, 39 femurs were fractured, and in the testing set, 13 were fractured.

Figure 6:
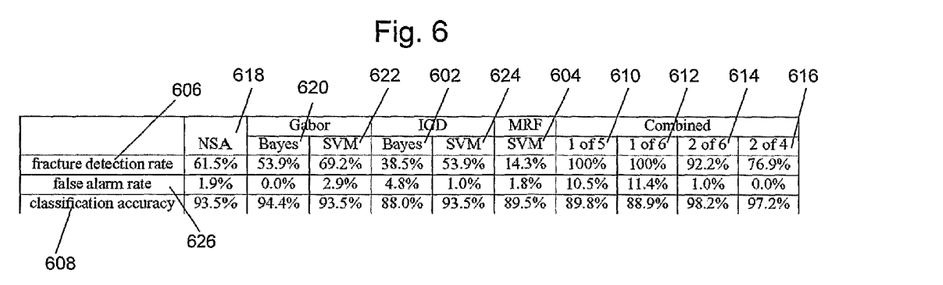
FIG. 6 shows test results of femur fracture detection according to an example embodiment.

FIG. 6 shows the table of results derived from the experiment above. Six different classifiers were trained: neck-shaft angle with thresholding (NSA) 618, Gabor texture with Bayesian classifier 620 and SVM 622, Intensity Gradient Direction (IGD) with Bayesian classifier 602 and SVM 624, and Markov Random Field texture with SVM 604. After training, they were applied on the testing samples and three performance measures were computed:
1) fracture detection rate 606: the number of correctly detected fractured samples over the number of fractured samples,
2) false alarm rate 626: the number of wrongly classified healthy samples over the number of healthy samples,
3) classification accuracy 608: the number of correctly classified samples over the total number of samples.

FIG. 6 illustrates that individual classifiers have rather low fracture detection rate 606, particularly IGD with Bayesian classifier 602 and MRF with SVM 604. However, due to the nature of their methods, each of them can detect some fractures that are missed by the other classifiers. So, by combining all the classifiers, both the fracture detection rate 606 and classification accuracy 608 can be improved significantly. It was found that the following combinations yield good performance:
"1-of-5" 610: A femur is classified as fractured if any one of the five classifiers, except MRF with SVM 604, classifies it as fractured.
"1-of-6" 612: A femur is classified as fractured if any one of the six classifiers classifies it as fractured.
"2-of-6" 614: A femur is classified as fractured if any two of the six classifiers classify it as fractured.
"2-of-4" 616: A femur is classified as fractured if any two of the following four classifiers classify it as fractured: neck-shaft angle method 618, Gabor texture with Bayesian classifier 620, Gabor texture with SVM 622, and intensity gradient direction with SVM 624.

Figure 7:
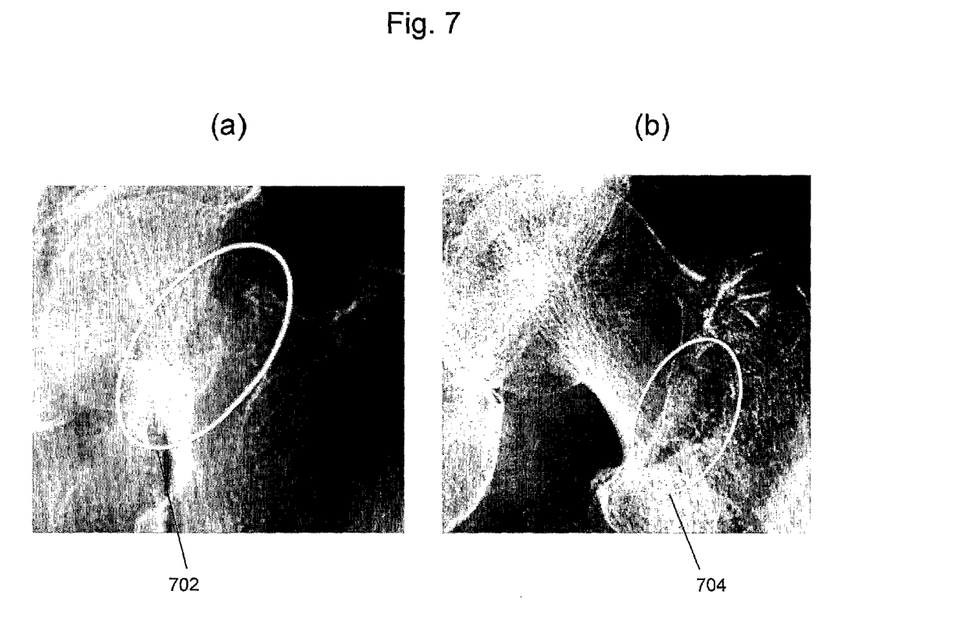
FIG. 7a shows subtle fractures at the femoral neck of a human femur in an x-ray image.
FIG. 7b shows subtle fractures at the femoral neck of another human femur in an x-ray image.

The "1-of-5" method 610 has the highest fracture detection rate 606 of 100%, which means every fracture can be detected by at least one of the classifiers. These detected fractures include very subtle fractures. Examples of subtle fractures in two different images of the femoral neck can be seen marked out by white ellipses 702 and 704 in FIGS. 7a and 7b respectively. The test results in FIG. 6 show that the six classifiers can indeed complement each other. The "1-of-6" method 612 also has a fracture detection rate 606 of 100% but a slightly higher false alarm rate 626 of 11.4%, resulting in a slightly lower overall classification accuracy 608 of 88.9%. This is due to the lower classification accuracy 608 of MRF with SVM 604 compared to most of the other methods. The 2-of-6 method 614 has the best overall performance of high fracture detection rate 606 (92.2%), low false alarm rate 626 (1.0%), and high classification accuracy 608 (98.2%). The "2-of-4" method 616 has no false alarm at all, at the expense of lower fracture detection rate 606 (76.9%) and slightly lower classification accuracy 608 (97.2%).

Another experiment on detecting fractures of the radius near the wrist was also performed using MRF texture model together with SVM classifier (604 in FIG. 6).

Figure 8:
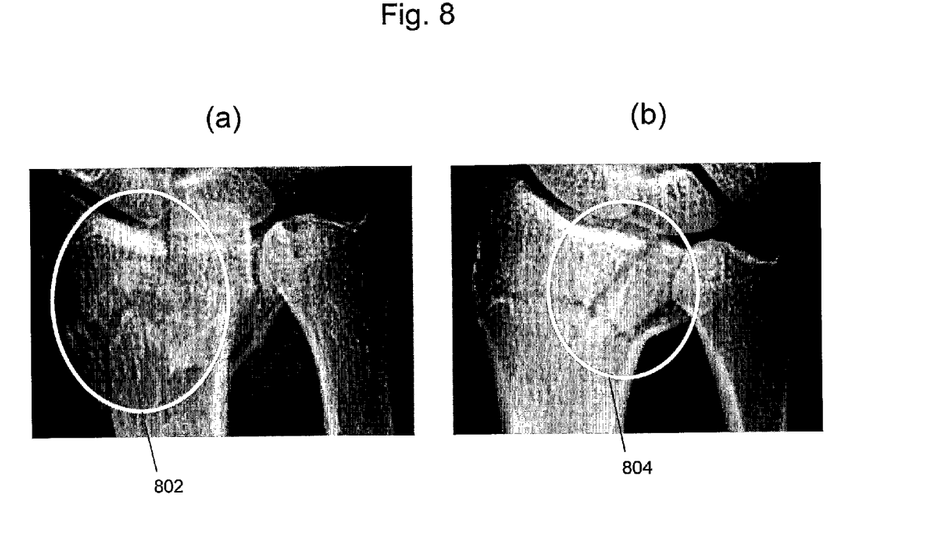
FIG. 8a shows radius fractures near a human wrist in an x-ray image.
FIG. 8b shows radius fractures near another human wrist in an x-ray image.

145 wrist images were obtained from the same local public hospital, and were divided randomly into 71 training and 74 testing images. In the training set, 21 radius bones were fractured whereas 23 were fractured in the testing set. FIGS. 8a and 8b show examples of radius fractures marked out in white ellipses 802 and 804.

Figure 9:
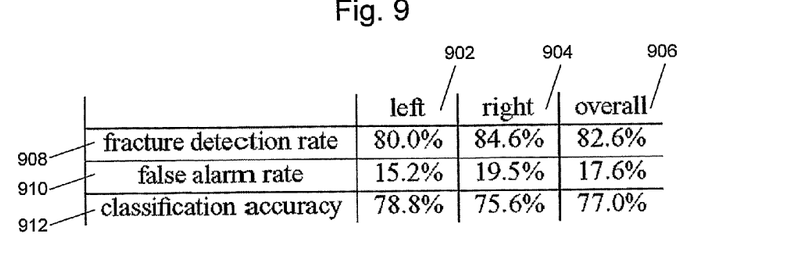
FIG. 9 shows the test results of radius fracture detection according to an example embodiment.

FIG. 9 shows the performance of the classifier on the testing samples. 'left' 902 indicates left wrist and 'right' 904 indicates right wrist and 'overall' 906 indicates the average results of the left and right wrist detection. As in FIG. 6, three performance measures, fracture detection rate 908, false alarm rate 910 and classification accuracy 912 are gauged. Interestingly, MRF with SVM (604 in FIG. 6) performed quite well in detecting radius fractures although it did not perform as well in detecting femur fractures. The reason could be that the fractures of the radius near the wrist are visually more obvious than those at the femoral neck, which can be very subtle (e.g. FIG. 8). It is expected that other feature-classifier combinations are able to complement MRF with SVM (604 in FIG. 6) for detecting radius fractures as well.

The example embodiment described above describes the detection of bone fractures in x-ray images. A suite of methods that combine different features and classification techniques have been developed and tested. Individual classifiers in the example embodiment can complement each other in fracture detection. As a result, by combining the individual classifiers, both fracture detection rate and classification accuracy can be improved significantly in preferred embodiments. Embodiments of the invention may be used in fracture detection for all kinds of bones.

In the described embodiments, adaptive sampling is used for the extraction of the features for classification. Adaptive sampling can adapt to the variation of size over different images. Another advantage of the adaptive sampling method is that it requires the extraction of only approximate bone contours. Therefore, it can also tolerate slight variation of shape over different patients, and does not require very accurate extraction of the bone contours.

Additionally, the described embodiments may be extended to fracture detection in the presence of growth plates of for example, the radius bone. Growth plates are a feature of the natural growing process of the radius. In some cases, growth plates can be in presence together with fractures of the radius further away from the wrist.

Figure 10:
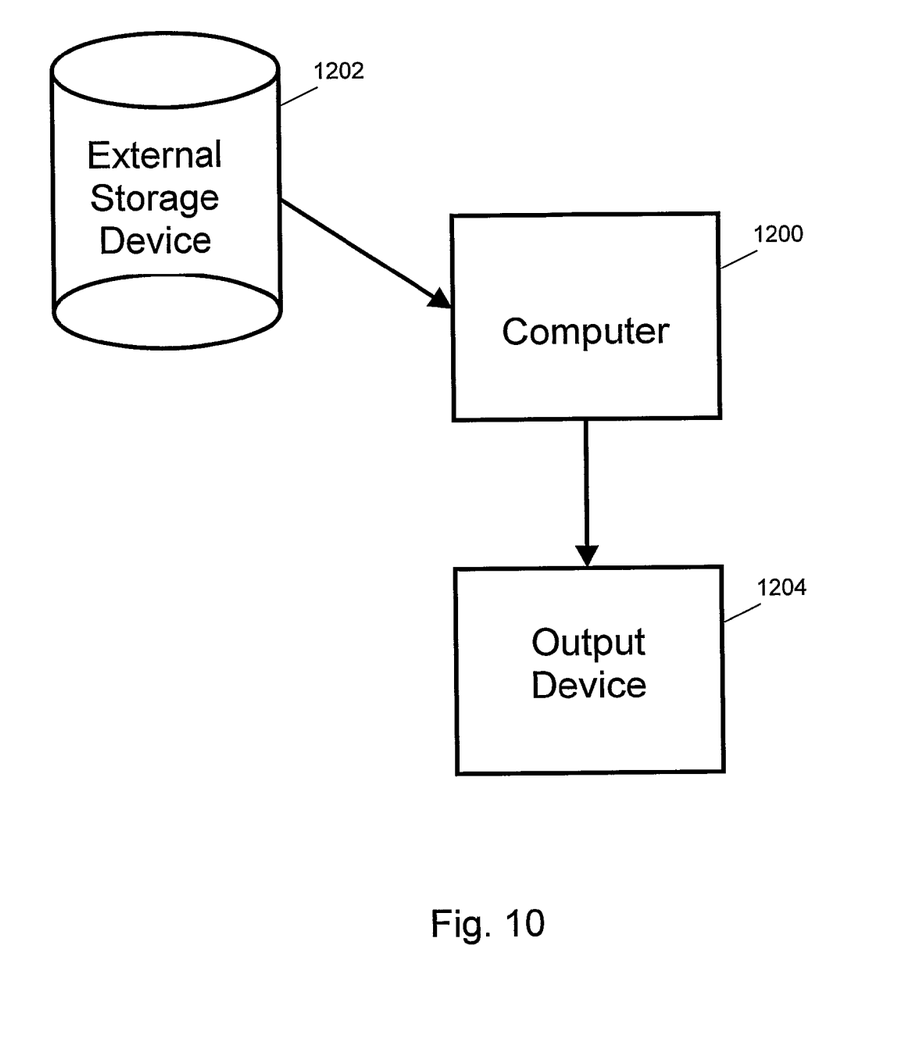
FIG. 10 shows the schematic diagram of a computer system implementation according to an example embodiment.

FIG. 10 shows the system view of the computer system implementation of an example embodiment of the present invention. The computer 1200 reads in digital x-ray images from an external storage device 1202, analyses the images, and displays the results on an output device 1204. The analyzing of the images refers to the 3 stages of the method of detecting fractures in the example embodiment: (1) extraction of approximate contour of the bone of interest, (2) extraction of features from the x-ray image, and (3) classification of the bone based on the extracted features, as described earlier.

Figure 11:
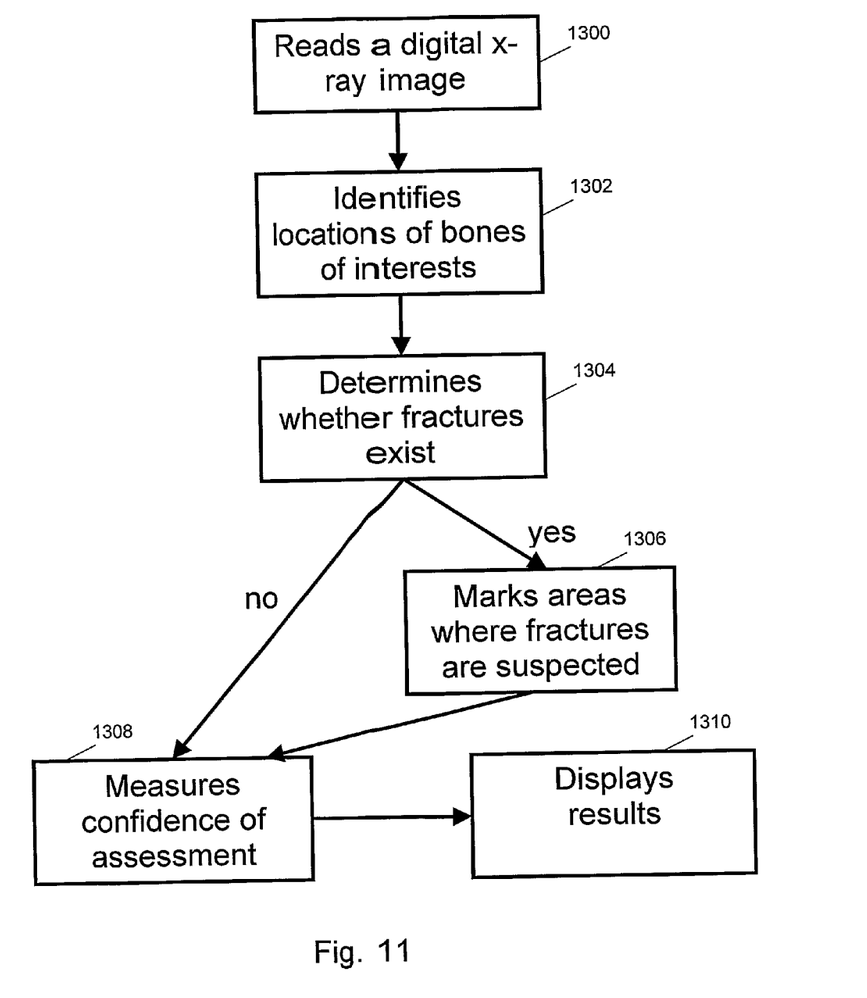
FIG. 11 shows a flow chart illustrating the processes implemented in the computer system of FIG. 10.

FIG. 11 is a flow chart illustrating the flow of processes in the computer (1200 in FIG. 10). In step 1300, the computer (1200 in FIG. 10) reads in an x-ray image. Next, in step 1302, the computer (1200 in FIG. 10) identifies the locations of the bones of interests. This corresponds with the stage of extraction of the approximate contour of the bone of interest, described in the example embodiments above.

In step 1304, the computer (1200 in FIG. 10) determines whether fractures exist in the bones of interests, based on the analysis described in the example embodiments above. If fractures exist, the areas of suspected fractures are marked out in step 1306. This is followed by measuring the confidence of the assessment of the suspected fractures in step 1308.

If fractures do not exist, the confidence of the assessment that no fractures exist is measured in step 1308. For example, for a newly processed image, the features described above are extracted and classified using Bayesian method and SVM. For Bayesian method, the probability P(fracture|x) is used as a confidence measure in the example embodiment. For SVM, the distance of the image's feature map to the hyperplane is used as a confidence measure in the example embodiment.

After the confidence of the assessment is measured, the analysis results are displayed on, for example, a computer monitor connected to the computer (1200 in FIG. 10) in step 1310. In addition, the analysis results such as those relating to the suspected fractures are alerted to the people examining the x-ray images (e.g. doctors) through manual alerts by the user of the system or electronic alerts such as email.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A method for detection of bone fractures using image processing of a digitized x-ray image, the method comprising:
    extracting a contour of a bone in the digitized x-ray image;
    identifying a bounding box around an area of interest based on the extracted contour of the bone; and
    applying an adaptive sampling scheme in which the bounding box is divided into a predetermined number of sampling points of a normalized sampling grid such that sampling locations in different images correspond to consistent locations within the area of interest.

2. The method as claimed in claim 1, wherein the extracting of the contour of the bone in the digitized x-ray image comprises applying a Canny edge detector to the digitized x-ray image.

3. The method as claimed in claims 1, wherein the extracting of the contour of the bone in the digitized x-ray image comprises applying a snake algorithm to the digitized x-ray image.

4. The method as claimed in claim 3, wherein applying the snake algorithm to the digitized x-ray image comprises creating a Gradient Vector Flow (GVF).

5. The method as claimed in claim 1, wherein a sampling region around the sampling points is chosen to cover image pixel points between the sampling points.

6. The method as claimed in claim 1, wherein the method further comprises calculating one or more texture maps of the digitized x-ray image and detecting a bone fracture based on respective reference texture maps.

7. The method as claimed in claim 6, wherein the texture maps comprise a Gabor texture orientation map.

8. The method as claimed in claim 6, wherein the texture maps comprise an Intensity gradient direction map.

9. The method as claimed in claim 6, wherein the texture maps comprise a Markov Random Field texture map.

10. The method as claimed in claim 6, wherein the method further comprises calculating one or more difference maps between the respective texture maps calculated for the digitized x-ray image and the respective reference texture maps.

11. The method as claimed in claim 10, wherein the difference maps are classified using one or more classifiers.

12. The method as claimed in claim 11, wherein the difference maps are classified using Bayesian classifiers.

13. The method as claimed in claim 11, wherein the difference maps are classified using Support Vector Machine classifiers.

14. The method as claimed in claim 1, wherein the processing method further comprises:
    determining a femoral shaft axis in the digitized x-ray image;
    determining a femoral neck axis in the digitized x-ray image;
    measuring an obtuse angle between the femoral neck axis and the femoral shaft axis; and
    detecting the bone fracture based on the measured obtuse angle.

15. The method as claimed in claim 14, further comprising calculating level lines from respective points on the contour of the bone in the digitized x-ray image and extending normally to the contour to respective other points on the extracted contour.

16. The method as claimed in claim 15, wherein determining the femoral shaft axis is based on midpoints of the level lines in a shaft portion of the contour of the bone.

17. The method as claimed in claim 15, wherein determining the femoral neck axis is based on the level lines in femoral head and neck portion of the contour of the bone.

18. A system for detection of bone fractures comprising:
    means for receiving a digitized x-ray image; and
    means for processing the digitized x-ray image for detection of bone fractures;
    wherein the means for processing the digitized x-ray image comprises
    means for extracting a contour of a bone in the digitized x-ray image,
    means for identifying a bounding box around an area of interest based on the extracted contour of the bone, and
    means for applying an adaptive sampling scheme in which the bounding box is divided into a predetermined number of sampling points of a normalized sampling grid such that sampling locations in different images correspond to consistent locations within the area of interest.

19. A system for detection of bone fractures comprising:
    a database for receiving and storing a digitized x-ray image; and
    a processor for processing the digitized x-ray image for detection of bone fractures, wherein the processor is configured to:
    extract a contour of a bone in the digitized x-ray image;
    identify a bounding box around an area of interest based on the extracted contour of the bone; and
    apply an adaptive sampling scheme in which the bounding box is divided into a predetermined number of sampling points of a normalized sampling grid such that sampling locations in different images correspond to consistent locations within the area of interest.

* * * * *